United States Patent
Mousavikhamene et al.

(10) Patent No.: US 10,058,505 B2
(45) Date of Patent: Aug. 28, 2018

(54) TRANSSCLERAL DRUG DELIVERY

(71) Applicants: Zeynab Mousavikhamene, Tehran (IR); Mohammad Jafar Abdekhodaie, Tehran (IR); Hamid Ahmadieh, Tehran (IR)

(72) Inventors: Zeynab Mousavikhamene, Tehran (IR); Mohammad Jafar Abdekhodaie, Tehran (IR); Hamid Ahmadieh, Tehran (IR)

( * ) Notice: Subject to any disclaimer, the term of this patent is extended or adjusted under 35 U.S.C. 154(b) by 213 days.

(21) Appl. No.: 14/975,767

(22) Filed: Dec. 19, 2015

(65) Prior Publication Data

US 2016/0101043 A1 Apr. 14, 2016

Related U.S. Application Data

(60) Provisional application No. 62/136,526, filed on Mar. 22, 2015.

(51) Int. Cl.
| | | |
|---|---|---|
| *A61K 9/14* | (2006.01) | |
| *A61K 9/16* | (2006.01) | |
| *A61N 2/08* | (2006.01) | |
| *A61K 9/00* | (2006.01) | |
| *A61F 9/00* | (2006.01) | |
| *A61K 9/51* | (2006.01) | |
| *A61N 2/00* | (2006.01) | |
| *A61K 9/50* | (2006.01) | |

(52) U.S. Cl.
CPC .......... *A61K 9/0009* (2013.01); *A61F 9/0017* (2013.01); *A61K 9/0048* (2013.01); *A61K 9/5161* (2013.01); *A61K 9/5094* (2013.01); *A61N 2/002* (2013.01)

(58) Field of Classification Search
CPC .......... A61N 2/00–2/12; A61K 9/0009; A61K 9/0048; A61K 9/1818–9/1887; A61K 9/5094
See application file for complete search history.

(56) References Cited

U.S. PATENT DOCUMENTS

| | | | |
|---|---|---|---|
| 2004/0086572 A1* | 5/2004 | Dailey | A61K 9/0043 424/489 |
| 2010/0121231 A1* | 5/2010 | Chow | A61H 5/00 601/46 |

(Continued)

OTHER PUBLICATIONS

Raghava et al., "Periocular routes for retinal drug delivery," Expert Opinion on Drug Delivery, 1:1, p. 99-114 (2004).*

(Continued)

*Primary Examiner* — Thaddeus Cox
(74) *Attorney, Agent, or Firm* — NovoTechIP International PLLC

(57) ABSTRACT

Magnetic drug-loaded polymeric particles are used in a transscleral drug delivery method. In the synthesis process of the aforementioned magnetic drug-loaded polymeric particles, therapeutic agents, along with a magnetic agent are encapsulated in a polymer. The aforementioned magnetic drug-loaded particles can be placed near the outer surface of the sclera, and then a magnetic field can be applied in front of the eye to pull these magnetic drug-loaded particles to the outer surface of the sclera, where these particles adhere to the outer surface of the sclera and thus, the orbital clearance of the particles is eliminated or reduced.

8 Claims, 11 Drawing Sheets

(56) References Cited

U.S. PATENT DOCUMENTS

| | | | |
|---|---|---|---|
| 2012/0265001 A1 | 10/2012 | Asmatulu et al. | |
| 2013/0017229 A1* | 1/2013 | Mooney | A61K 9/0009 424/400 |
| 2013/0225906 A1* | 8/2013 | Zysler | A61F 9/007 600/12 |
| 2013/0296632 A1 | 11/2013 | Whitmore | |
| 2015/0305929 A1* | 10/2015 | Goldberg | G02B 1/043 604/521 |
| 2015/0374543 A1* | 12/2015 | Shapiro | A61F 9/0026 600/12 |

OTHER PUBLICATIONS

Dengler et al., Targeted Delivery of Magnetic Cobalt Nanoparticles to the Eye Following Systemic Administration, AIP Conference Proceedings 1311, 329 (2010).*

Kompella et al., "Nanomedicines for Back of the Eye Drug Delivery, Gene Delivery, and Imaging," Prog. Retin. Eye Res., 36: 172-198 (Sep. 2013).*

Gianni Ciofani, Magnetic alginate microspheres: system for the position controlled delivery of nerve growth factor, Biomedical Microdevices, vol. 11, Issue 2, pp. 517-527.

M.A. Morales, In situ synthesis and magnetic studies of iron oxide nanoparticles in calcium-alginate matrix for biomedical applications, Materials Science and Engineering: C, vol. 28, Issue 2, Mar. 10, 2008, pp. 253-257.

Hemalatha B. Raju, Evaluation of Magnetic Micro- and Nanoparticle Toxicity to Ocular Tissues, PLoS One, vol. 6, Issue 5, e17452.

Urs O. Hafeli, Cell Uptake and in Vitro Toxicity of Magnetic Nanoparticles Suitable for Drug Delivery, Molecular Pharmaceutics, vol. 6, Issue 5, May 15, 2009, pp. 1417-1428.

Martina Giannaccini, Magnetic Nanoparticles as Intraocular Drug Delivery System to Target Retinal Pigmented Epithelium (RPE), International Journal of Molecular Sciences, vol. 15, Issue 1, 2014, pp. 1590-1605.

* cited by examiner

TRANSSCLERAL DRUG DELIVERY

CROSS REFERENCE TO RELATED APPLICATION

This application claims the benefit of priority from U.S. Provisional Patent Application Ser. No. 62/136,526, filed on Mar. 22, 2015, and entitled "Facilitation of Transsclera Drug Delivery Using Drug-loaded Magnetic Polymeric Particles," which is incorporated by reference herein in its entirety.

SPONSORSHIP STATEMENT

This application has been sponsored by the Iranian Nanotechnology Initiative Council, which does not have any rights in this application.

TECHNICAL FIELD

The present application generally relates to transscleral delivery of therapeutic agents to the eye. The present application specifically relates to a method for sustained and targeted transscleral delivery of drugs to the eye.

BACKGROUND

In transscleral drug delivery method, drug is entered in the periocular space of the eye, precisely against the outer region of the sclera. Transscleral drug delivery is considered as a promising route of ocular drug delivery due to the large surface area of the sclera (which is approximately 16.3 $cm^2$), its porosity and fewer enzymatic activities to degrade drug, compared to the cornea. Despite all these advantages, some obstacles adversely affect the efficiency of transscleral route, such as orbital clearance, intraocular pressure, uveoscleral outflow, choroidal blood flow, and the blood-retinal barriers. Currently, one of the main obstacles of the transscleral drug delivery is the drug removal by inevitable bulk fluid flow in the back of the eye, and an eventual clearance by vasculature of conjunctive or choroid.

Hence, there is a need in the art for a transscleral drug delivery method to reduce the orbital clearance of drugs, which are administered transsclerally for the treatment of the diseases of the eye.

SUMMARY

In one general aspect, the instant application describes a method for transscleral drug delivery, in which the orbital clearance of drugs from the posterior segment of the eye, is reduced or eliminated, and as a result, transfer of a therapeutically effective amount of drugs through the sclera is enabled.

In the method introduced in this disclosure, magnetic drug-loaded polymeric particles are used in the transscleral drug delivery. In the synthesis process of the aforementioned magnetic drug-loaded polymeric particles, therapeutic agents, along with a magnetic agent are encapsulated in a polymer. These particles respond to magnetic fields due to the presence of the magnetic agent in their composition. The aforementioned magnetic drug-loaded particles can be placed near the outer surface of the sclera, and then a magnetic field can be applied in front of the eye to pull these magnetic drug-loaded particles to the outer surface of the sclera, and hold the particles in that region, and thus, eliminating or reducing the orbital clearance of the particles from the posterior segment of the eye. The magnetic field holds the drug-loaded magnetic particles on the outer surface of the sclera, and, as a result, the exposure of the sclera to the drug, which is released form the aforementioned magnetic drug-loaded particles is prolonged, and therefore, the transfer of a therapeutically effective amount of the drug through the sclera is enabled, which solves an important issue associated with transscleral drug-delivery, especially for the treatment of chronic diseases of the eye.

In one implementation, the polymer used to encapsulate the therapeutic agents and the magnetic agent can be, for example, a bio-adhesive polymer, such as sodium alginate. In this implementation, the magnetic drug-loaded particles not only respond to a magnetic field due to the presence of a magnetic agent in their composition, but also are capable of adhering to the outer surface of the sclera, due to their bio-adhesive polymeric carrier.

Iron oxide nanoparticles can be used as the magnetic agent, which makes the drug-loaded particles responsive to magnetic fields.

Any compounds and compositions currently known or yet to be discovered that are useful in treating or preventing the diseases, disorders, and unwanted conditions of the eye, may be considered as the therapeutic agent.

In one general aspect, the instant application describes a method for transscleral drug delivery. The method includes steps of placing magnetic drug-loaded polymeric particles in a posterior segment of an eye, near an outer surface of a sclera; and applying a magnetic field in front of the eye to pull the magnetic drug-loaded polymeric particles closer to the outer surface of the sclera.

The above general aspect may include one or more of the following features. Placing the magnetic drug-loaded polymeric particles may include injecting the magnetic drug-loaded polymeric particles into the posterior segment of the eye, near the outer surface of the sclera. The magnetic drug-loaded polymeric particles may include a therapeutic agent and a magnetic agent encapsulated in a polymer. The magnetic agent may be selected from a group consisting of nanoparticles of iron oxides.

The polymer may be selected from a group consisting of polyvinyl pyrrolidone of various molecular weights, cellulose, cellulose derivatives, cellulose esters, gums, polyethylene oxides, hyaluronic acid, carbopol polymers, chitosan, pectin, gelatin, or mixtures thereof. The magnetic drug-loaded polymeric particles may include a therapeutic agent and a magnetic agent encapsulated in a bio-adhesive polymer. The bio-adhesive polymer may be sodium alginate. The therapeutic agent may be selected from a group consisting of vascular endothelial growth factor (VEGF) receptor kinase inhibitors, pyrrolidine, dithiocarbamate; squalamine; TPN 470 analogue and fumagillin; protein kinase C inhibitors; thiazolidinediones; cyclooxygenase inhibitors; proteosome inhibitors; pegaptanib; vitronectin receptor antagonists; $\alpha$-v/$\beta$-3 integrin antagonists; $\alpha$-v/$\beta$-1 integrin antagonists; Tie-1 and Tie-2 kinase inhibitors; interferon, including $\gamma$-interferon or interferon targeted to CNV by use of dextran and metal coordination; pigment epithelium derived factor (PEDF); endostatin; tetrathiomolybdate; angiostatin; anecortave acetate; tumistatin; acetonide; triamcinolone; RNA silencing or RNA interference (RNAi) of angiogenic factors, including ribozymes that target VEGF expression; canstatin; (isotretinoin) Accutane™ (13-cis retinoic acid); ACE inhibitors, including but not limited to quinopril, captopril, and perindozril; inhibitors of mTOR; 3-aminothalidomide; pentoxifylline; 2-methoxyestradiol; colchicines; AMG-1470; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; (verteportin) Visudyne™, snET2 and other photo sensitizers; inhibitors of hepatocyte growth factor; antibiotics; antiviral agents; and anesthetics.

In another general aspect, the instant application describes a method that includes steps of injecting magnetic drug-loaded polymeric particles in a posterior segment of an eye, near an outer surface of a sclera, wherein the magnetic drug-loaded polymeric particles include a therapeutic agent and a magnetic agent encapsulated in a polymer; and applying a magnetic field in front of the eye to bring the magnetic drug-loaded polymeric particles in direct contact with outer surface of the sclera to reduce clearance of particles from periocular route and deliver a therapeutically effective amount of the therapeutic agent to the eye for an extended period.

The above general aspect may include one or more of the following features. Injecting the magnetic drug-loaded polymeric particles may include injecting the magnetic drug-loaded polymeric particles via a syringe. The polymer may include a bio-adhesive polymer. The bio-adhesive polymer may be sodium alginate. The magnetic drug-loaded polymeric particles may be configured to adhere to the outer surface of the sclera, due to the bio-adhesive polymer acting as a carrier for the magnetic drug-loaded polymeric particles. The magnetic agent may be selected from a group consisting of nanoparticles of iron oxides. The polymer may be selected form a group consisting of polyvinyl pyrrolidone of various molecular weights, cellulose, cellulose derivatives, cellulose esters, gums, polyethylene oxides, hyaluronic acid, carbopol polymers, chitosan, pectin, gelatin, or mixtures thereof.

In another general aspect, the instant application describes injecting magnetic drug-loaded polymeric particles in a posterior segment of an eye, near an outer surface of a sclera. The magnetic drug-loaded polymeric particles include a therapeutic agent and a magnetic agent encapsulated in a bio-adhesive polymer. The magnetic drug-loaded polymeric particles are configured to respond to a magnetic field due to a presence of the magnetic agent and as a result being pulled closer to the outer surface of the sclera and to adhere to the outer surface of the sclera due to a presence of the bio-adhesive polymer acting as a carrier for the magnetic drug-loaded polymeric particles.

The above general aspect may include one or more of the following features. The method may further include applying the magnetic field in front of the eye to bring the magnetic drug-loaded polymeric particles in direct contact with outer surface of the sclera to reduce clearance of particles from periocular route and deliver a therapeutically effective amount of the therapeutic agent to the eye for an extended period. Injecting the magnetic drug-loaded polymeric particles may include injecting the magnetic drug-loaded polymeric particles via a syringe. The bio-adhesive polymer may be sodium alginate. The magnetic agent may be selected from a group consisting of nanoparticles of iron oxides.

BRIEF DESCRIPTION OF THE DRAWINGS

FIG. 1A illustrates injecting the magnetic drug-loaded polymeric particles near the outer surface of the sclera; and FIG. 1B illustrates applying a magnetic field in front of the eye to pull the magnetic drug-loaded particles to the outer surface of the sclera.

DETAILED DESCRIPTION

Figure 1A:
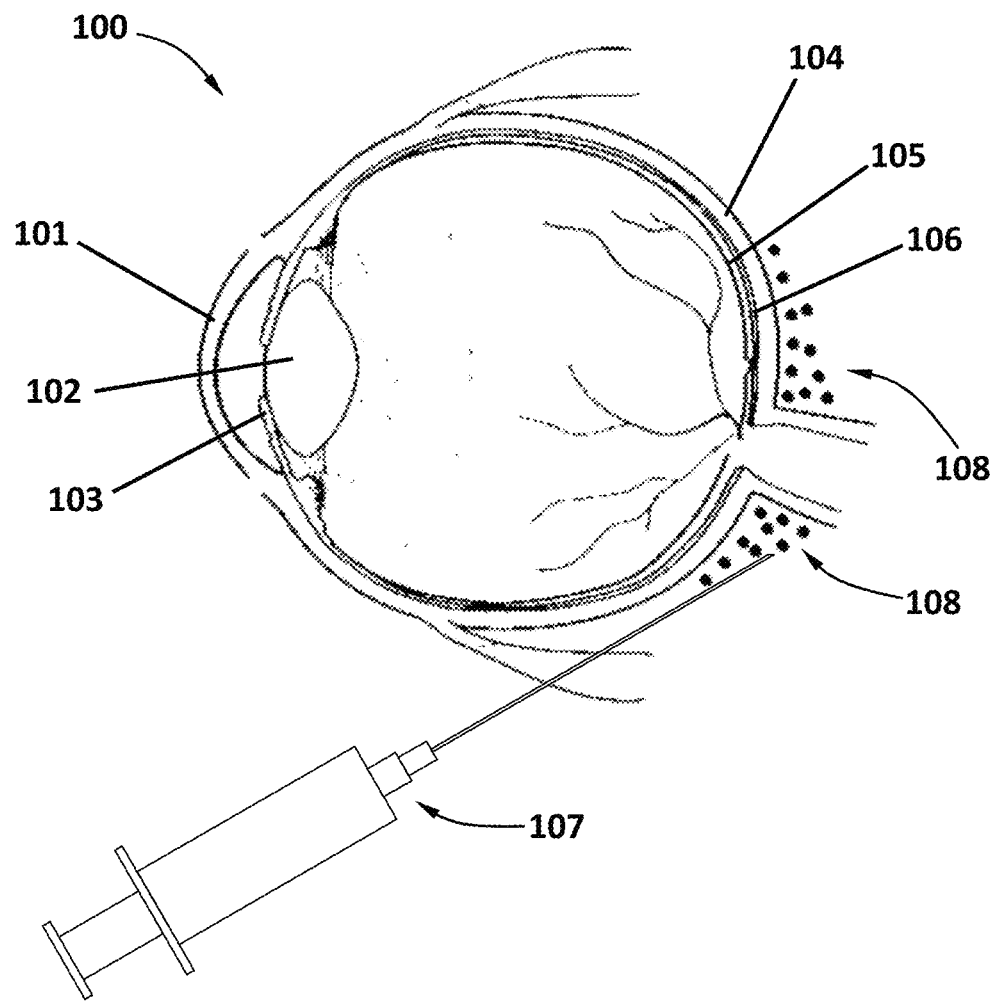
FIGS. 1A-1B illustrate exemplary and non-limiting schematic representation of transscleral drug delivery method of the present application. Specifically.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. The present application is not intended to be limited to the implementations shown, but is to be accorded the widest possible scope consistent with the principles and features disclosed herein.

Described in this application is a method for the transscleral delivery of therapeutic agents to the eye. The present application specifically introduces a method for sustained targeted delivery of therapeutic agents to the eye. This method can be used for the treatment and prevention of diseases and unwanted conditions of the posterior segment of the eye, including but not limited to choroidal neovascularization; macular degeneration; age-related macular degeneration, including wet AMD; retinal angiogenesis; chronic uveitis; and other retino-proliferative conditions.

The transscleral drug delivery method of the instant application can eliminate or reduce the orbital clearance of drugs. The orbital clearance of drugs is one of the well-known drawbacks of transscleral drug delivery systems, which prevents the transfer of a therapeutically effective amount of the drug through the sclera.

The transscleral drug delivery method of the instant application is configured to provide a sustained targeted delivery of therapeutic agents to the eye. In one implementation, magnetic drug-loaded polymeric particles are used in the transscleral drug delivery method of the instant application. The aforementioned magnetic drug-loaded polymeric particles include a drug carrier, a magnetic agent, and a therapeutic agent. A polymer is used as the drug carrier, in which the magnetic agent and the therapeutic agent are encapsulated. Iron oxide nanoparticles, such as $Fe_2O_3$, $Fe_3O_4$, or $Fe_2O_4$ nanoparticles, may be used as the magnetic agent. Compounds and compositions currently known or yet to be discovered that are useful in treating and preventing the diseases and unwanted conditions of the eye, may be considered as the therapeutic agent.

In one implementation, the magnetic drug-loaded particles may be injected in the periocular space of the eye. In another implementation, the magnetic drug-loaded particles may be injected in the back of the eye to the orbital side, and against and/or within vicinity of the outer surface of the sclera. Then, by applying a magnetic field in front of the eye, the magnetic force pulls the magnetic drug-loaded polymeric particles to the outer surface of the sclera. In one implementation, the magnetic field holds the drug-loaded magnetic particles directly on the outer surface of the sclera. As a result, the clearance of particles from periocular route is reduced or eliminated. Therefore, a therapeutically effective amount of the therapeutic agent can be delivered to the eye for an extended period.

In one implementation, the polymer, which is used to encapsulate the therapeutic agents and the magnetic agent can be, for example, a bio-adhesive polymer, such as sodium alginate. In this implementation, the magnetic drug-loaded particles not only respond to a magnetic field due to the presence of a magnetic agent in their composition, but also are capable of adhering to the outer surface of the sclera, due to their bio-adhesive polymeric carrier.

The polymers, which are used to encapsulate the therapeutic agents and the magnetic agent, include but are not limited to: polyvinyl pyrrolidone of various molecular weights; celluloses, such as ethyl cellulose, methyl cellulose, microcrystalline cellulose, etc.; cellulose derivatives, such as hydroxy ethyl cellulose, carboxy methyl cellulose, hydroxypropyl methyl cellulose, etc.; cellulose esters, such as cellulose acetate, cellulose acetate butyrate, cellulose acetate propionate, etc.; gums, such as guar gum, xanthan gum, karaya gum, tragacanth, gum *arabica*, etc.; polyethylene oxides, such as polyox and polyethylene glycol, etc.; hyaluronic acid and its derivatives; carbopols; chitosan and soluble starch; pectin; gelatin; or mixtures thereof.

In some implementations, a cross-linking agent, such as calcium chloride, can be used in the synthesis of the polymeric particles for cross-linking the polymer chains, and further strengthening the polymeric gel network.

It should be understood that generally, any compounds and compositions currently known or yet to be discovered that are useful in treating and preventing the diseases and unwanted conditions of the eye, may be considered as the "therapeutic agent". The therapeutic agents or the drugs include, but are not limited to: vascular endothelial growth factor (VEGF) receptor kinase inhibitors, pyrrolidine, dithiocarbamate (NF.kappa.B inhibitor); squalamine; TPN 470 analogue and fumagillin; PKC (protein kinase C) inhibitors; thiazolidinediones, such as rosiglitazone or troglitazone; cyclooxygenase inhibitors, such as diclofenac, vioxx, rofecoxib, nepafenac and celecoxib; proteosome inhibitors, such as Velcade™ (bortezomib, for injection; ranibuzumab (Lucentis™); pegaptanib (Macugen™); vitronectin receptor antagonists, such as cyclic peptide antagonists of vitronectin receptor-type integrins; α-v/β-3 integrin antagonists; α-v/β-1 integrin antagonists; Tie-1 and Tie-2 kinase inhibitors; interferon, including γ-interferon or interferon targeted to CNV by use of dextran and metal coordination; pigment epithelium derived factor (PEDF); endostatin; tetrathiomolybdate; angiostatin; anecortave acetate; tumistatin; acetonide; triamcinolone; RNA silencing or RNA interference (RNAi) of angiogenic factors, including ribozymes that target VEGF expression; can statin; (isotretinoin) Accutane™ (13-cis retinoic acid); ACE inhibitors, including but not limited to quinopril, captopril, and perindozril; inhibitors of mTOR; 3-aminothalidomide; pentoxifylline; 2-methoxyestradiol; colchicines; AMG-1470; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; (verteportin) Visudyne™, snET2 and other photo sensitizers; inhibitors of hepatocyte growth factor (antibodies to the growth factor or its receptors; small molecular inhibitors of the c-met tyrosine kinase; truncated versions of HGF e.g. NK4); antibiotics; antiviral agents; and anesthetics.

It should also be understood that a "therapeutically effective amount," of a therapeutic agent or a drug for administration, is that amount of the therapeutic agent or the drug that provides the therapeutic effect sought, when administered to a subject. As used herein, a "subject" is generally any living subject with an eye including but not limited to an animal or a human. The animal may include a veterinary animal or a model experimental animal that may benefit from administration of the therapeutic agents.

The method for transscleral drug delivery described in this disclosure has two steps. The first step may include delivering the magnetic drug-loaded polymeric particles to the posterior segment of the eye. The magnetic drug-loaded polymeric particles may be delivered to the posterior segment of the eye by for example injecting the drug-loaded polymeric particles to the posterior segment of the eye. The injection may be performed by a syringe. The second step of the transscleral drug delivery method may include applying a magnetic field in front of the eye using a device capable of providing a magnetic field. The device may include a magnet.

Figure 1B:
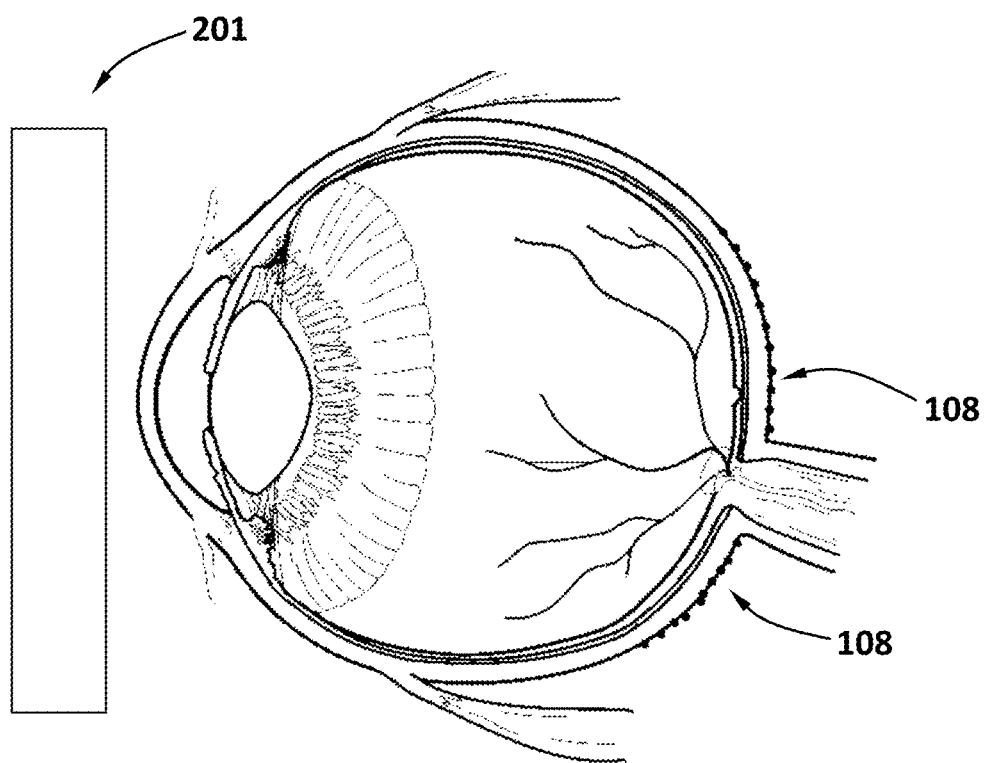
Figure 2A:
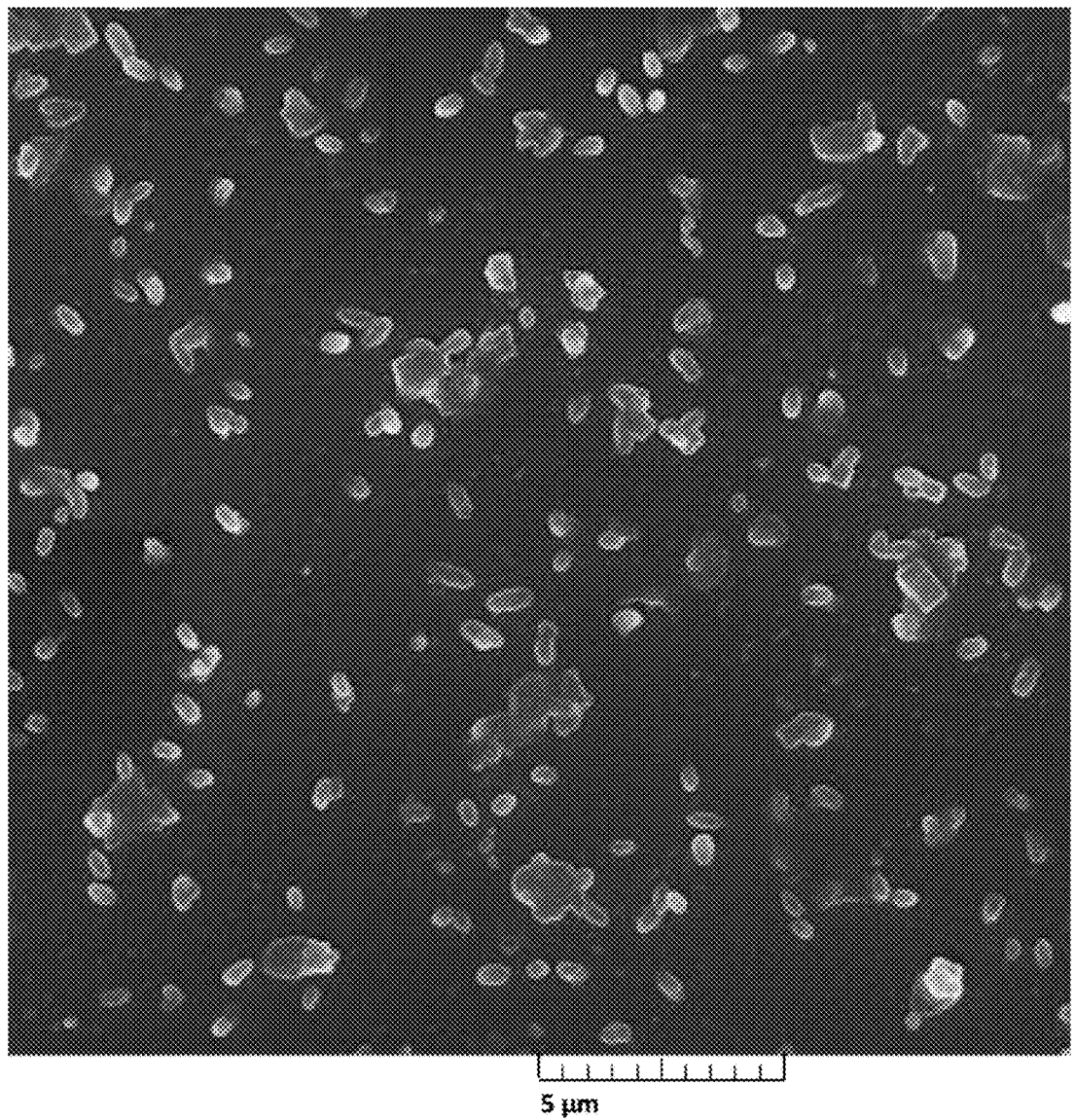
FIGS. 2A-2D illustrate the scanning electron microscope (SEM) images of exemplary magnetic drug-loaded polymeric particle samples, prepared as described in more detail in connection with example 1: sample 01 (FIG. 2A); sample 02 (FIG. 2B); sample 03 (FIG. 2C); and sample 04 (FIG. 2D).
Figure 2B:
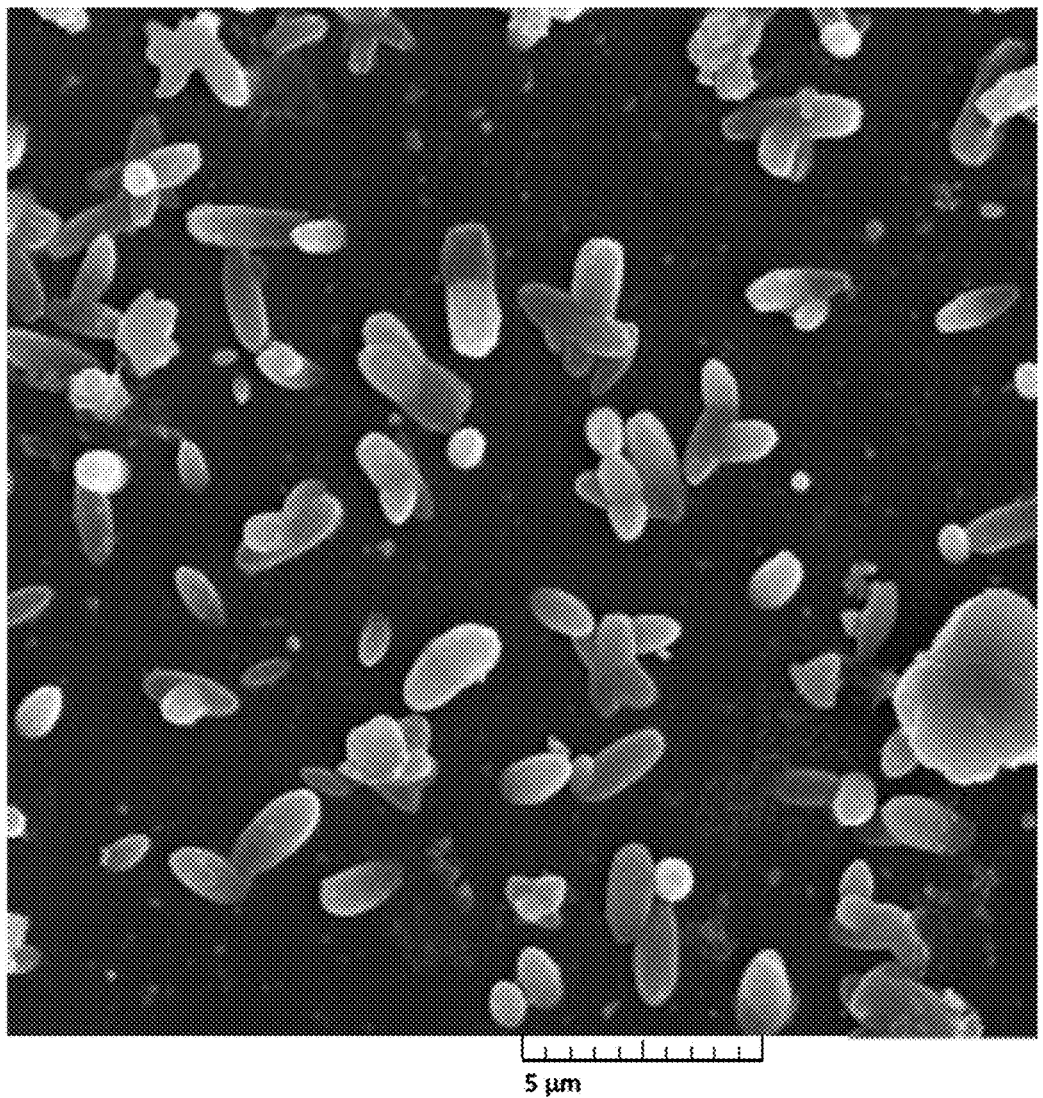
Figure 2C:
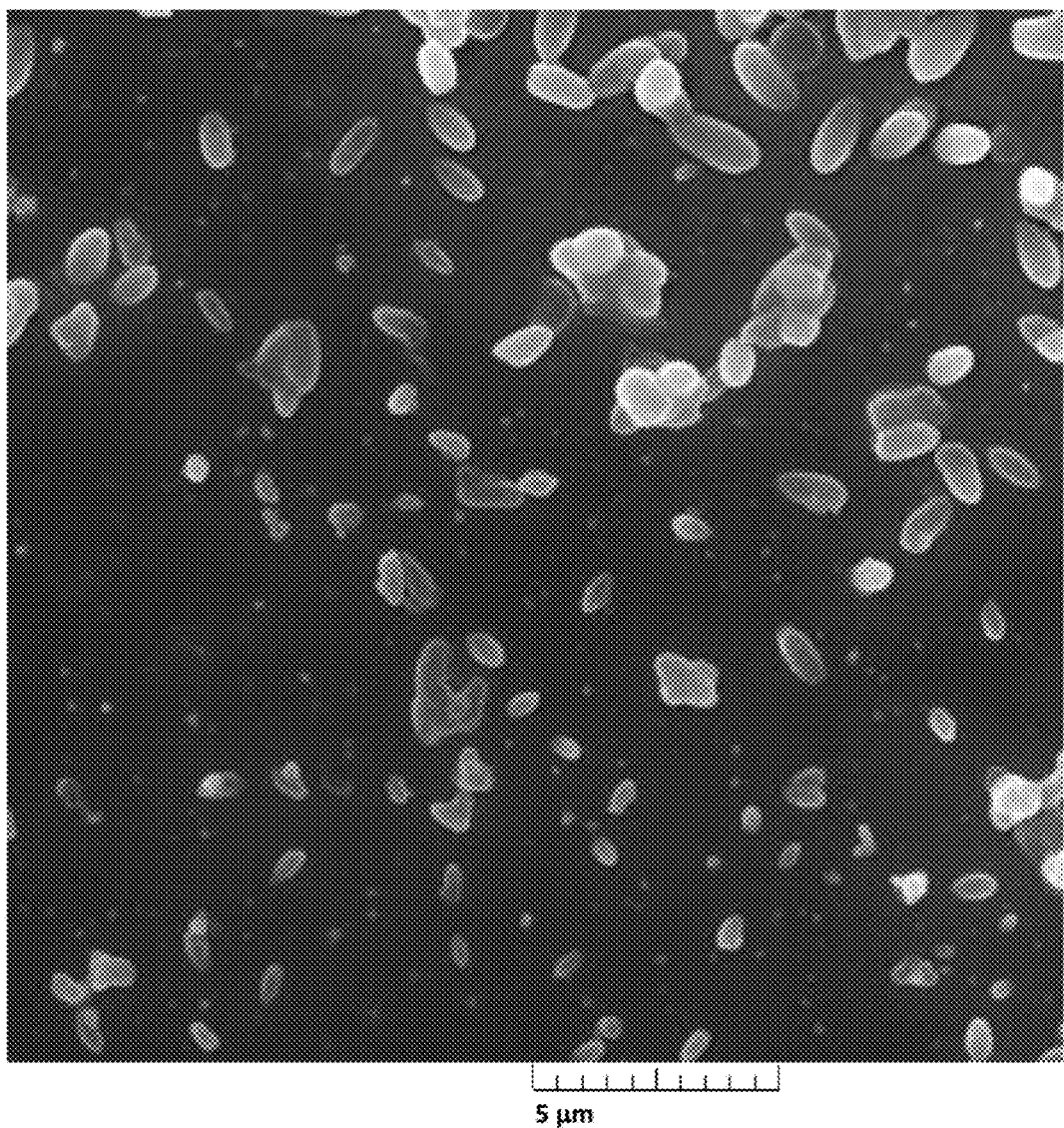
Figure 2D:
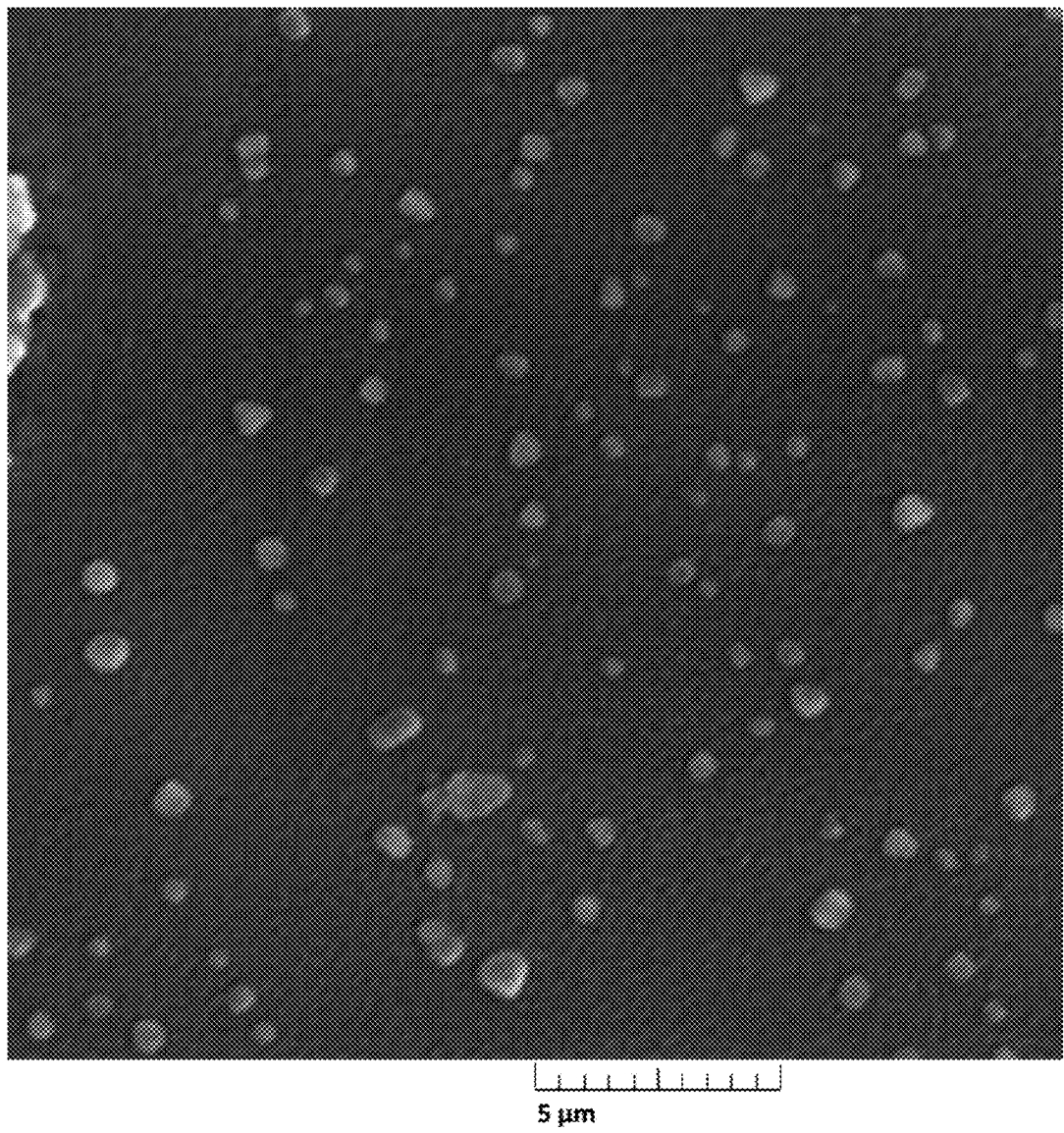

FIGS. 1A and 1B illustrate an exemplar and non-limiting schematic representation of the transscleral drug delivery method of the present application, where the magnetic drug-loaded polymeric particles are injected into the posterior segment of the eye. FIG. 1A shows different parts of an eye 100, including the cornea 101, lens 102, iris 103, sclera 104, choroid 105, and retina 106. In the first step of the transscleral drug delivery method, a specific amount of the magnetic drug-loaded polymeric particles 108 are injected near (adjacent, as depicted) the outer surface of the sclera 104 using an injector 108.

FIG. 1B shows an exemplar and non-limiting schematic representation of the second step of the transscleral drug delivery method of the present application. In the second step, a device 201 is used to apply a magnetic field in front of the eye. The magnetic drug-loaded polymeric particles 108 are pulled towards the outer surface of the sclera 104 under the uniform magnetic field. The magnetic field holds the drug-loaded magnetic particles 108 on the outer surface of the sclera 104, and as a result, the clearance of particles from periocular route is reduced or eliminated and a therapeutically effective amount of the therapeutic agent can be delivered for an extended period. In one implementation, the magnetic field holds the drug-loaded magnetic particles 108 directly on the outer surface of the sclera 104 such that the drug-loaded magnetic particles 108 remain in contact with the outer surface of the sclera.

In another implementation, in addition to the magnetic agent, a bio-adhesive polymer can be used to encapsulate the therapeutic agents and the magnetic agent. In this implementation, the magnetic drug-loaded particles not only respond to a magnetic field due to the presence of a magnetic agent in their composition, but also are capable of adhering to the outer surface of the sclera, due to their bio-adhesive polymeric carrier.

It should be understood, that in some implementations of the method described in this application, where bio-adhesive polymers are used to encapsulate the therapeutic agents and the magnetic agent, the presence of the magnetic field is necessary for pulling the drug-loaded particles to the outer surface of the sclera, but when the particles adhere to the outer surface of the sclera, due to their bio-adhesive polymeric carrier, the presence of the magnetic field is no longer necessary. After removing the magnetic field, the particles remain in their desirable positions in the outer surface of the sclera and therapeutically effective amounts of the drug, which is encapsulated in the particles, are released and transferred through the sclera.

The concentration of the therapeutic agent encapsulated in the magnetic drug-loaded particles is dependent on the strategy of the treatment. Hence, depending on the disease or disorder, which is being treated, different concentrations of the therapeutic agent or drug can be encapsulated in the magnetic polymeric particles. The concentration may be determined based on the application, the release rate and release profile or other variables determined by a physician.

The method for transscleral drug delivery introduced in this application may be used in treatment of different diseases of the eye, including but not limited to: ocular neovascularization, which includes but not limited to proliferative retinopathies, choroidal neovascularization (CNV), macular degeneration or age-related macular degeneration (AMD), diabetic and other ischemia-related retinopathies, diabetic macular edema, pathological myopia, myopic degeneration, von Hippel-Lindau disease, histoplasmosis of the eye, central retinal vein occlusion (CRVO), corneal neovascularization, and retinal neovascularization (RNV); tumor-caused neovasculization; eye diseases associated with inflammation, which include but are not limited to uveitis, chronic uveitis, endophthalmitis, ophthalmic trauma or surgery, retinitis, choroiditis; and optic neuritis or infectious eye diseases, such as HIV retinopathy, toxocariasis, toxoplasmosis, and endophthalmitis.

EXAMPLE 1

Preparation of Magnetic Drug-Loaded Alginate Particles

In this example, first, sodium alginate is dissolved in 10 ml of distilled water. Then, diclofenac sodium as an exemplar therapeutic agent and iron oxide nanoparticles, as the magnetic agent, are dispersed in the sodium alginate solution. After that, the resultant mixture is added dropwise to a solution, which contains 50 ml of isooctane and tween 80, as a surfactant, under homogenization at a speed of about 24000 rpm. Gelation is carried out by dropwise addition of 20 ml of 0.5 gr/ml $CaCl_2$ aqueous solution (cross-linking agent) and then 5 ml of 1 gr/ml $CaCl_2$ solution (cross-linking agent) under homogenization at 24000 rpm. The resultant magnetic drug-loaded particles are washed with distilled water and centrifuged three times. Finally, the particles are freeze dried. Different concentrations of the polymer, the magnetic agent and the therapeutic agent can be used to synthesize the magnetic drug-loaded polymeric particles. Furthermore, a higher (surfactant to organic phase) ratio can also be used to synthesize samples with smaller average particle size. Four different samples are prepared to determine the effect of different factors, such as the strength of the polymeric gel network, average particle size, and the presence of the magnetic agent, on the kinetics of drug release from the magnetic drug-loaded polymeric particles. Table 1, shows the characteristics of four different magnetic drug-loaded polymeric particles (labeled as Samples 01-04), synthesized pursuant to the teachings of the present application. Sample 01 is synthesized using a high concentration of the polymer solution, and the particles in this sample include the magnetic agent. Sample 02 is synthesized with the same concentration of the polymer solution, and with the same (surfactant to the organic phase) ratio, which means the average particle size of sample 02 is the same as that of sample 01. However, the particles of sample 02 are synthesized without the magnetic agent. Sample 03 is synthesized with a lower concentration of the polymer, which means the polymeric gel network of this sample is weaker than the other samples. Sample 03 has the same average particle size as samples 01 and 02, and it contains the magnetic agent. Finally, sample 04 is synthesized with the same concentration of the polymeric solution as samples 01 and 02, but the average particle size of this sample is smaller than that of the other three samples, since a higher (surfactant to the organic phase) ratio is used in the synthesis process of this sample.

TABLE 1

| Sample | Na alginate solution (wt %) | Surfactant:organic phase ratio | Magnetic agent weight (mg) |
|---|---|---|---|
| Sample 01 | 2 | 2:50 | 40 |
| Sample 02 | 2 | 2:50 | Without magnetic agent |
| Sample 03 | 1 | 2:50 | 40 |
| Sample 04 | 2 | 5:50 | 40 |

EXAMPLE 2

Characterization of the Synthesized Particles

In this example, 10 mg of each of the samples 01 to 04, synthesized as described in more detail in connection with example 1, are dispersed in 50 ml of phosphate buffer solution (PBS) and sonicated for 1 hour. Then, the resultant mixtures are shook for 24 hours, and then, they are centrifuged. The drug content in the supernatant solution is determined by a UV spectrophotometer at $\lambda=276$ nm. The drug encapsulation efficiency is calculated by the following equation:

Drug encapsulation efficiency %=(weight of the releasable drug/weight of the drug in the particles)×100.

FIGS. 2 A-D illustrate the scanning electron microscope (SEM) images of samples 01-04, respectively. These SEM images show that particles of samples 01-03 are almond shaped, and particles of sample 04 are smaller and spherical. Particle size distribution of sample 04 is more uniform. As can be seen in Table 1, more surfactant is used in the preparation of sample 04 compared to the other three samples, which has led to a decrease in particle size. Moreover, the use of more surfactant has made the particles spherical and more uniform. According to the SEM images illustrated in FIGS. 2 A-D, the average particle sizes of samples 01-04 are about 417.83 nm, 811.54 nm, 640.89 nm, and 60.29 nm, respectively.

Since no magnetic agent is used in the synthesis of sample 02, and since iron oxide nanoparticles act as a surfactant and reduce the surface tension of the solution, the average particle size of sample 01 is almost half of the average particle size of sample 02.

Figure 3:
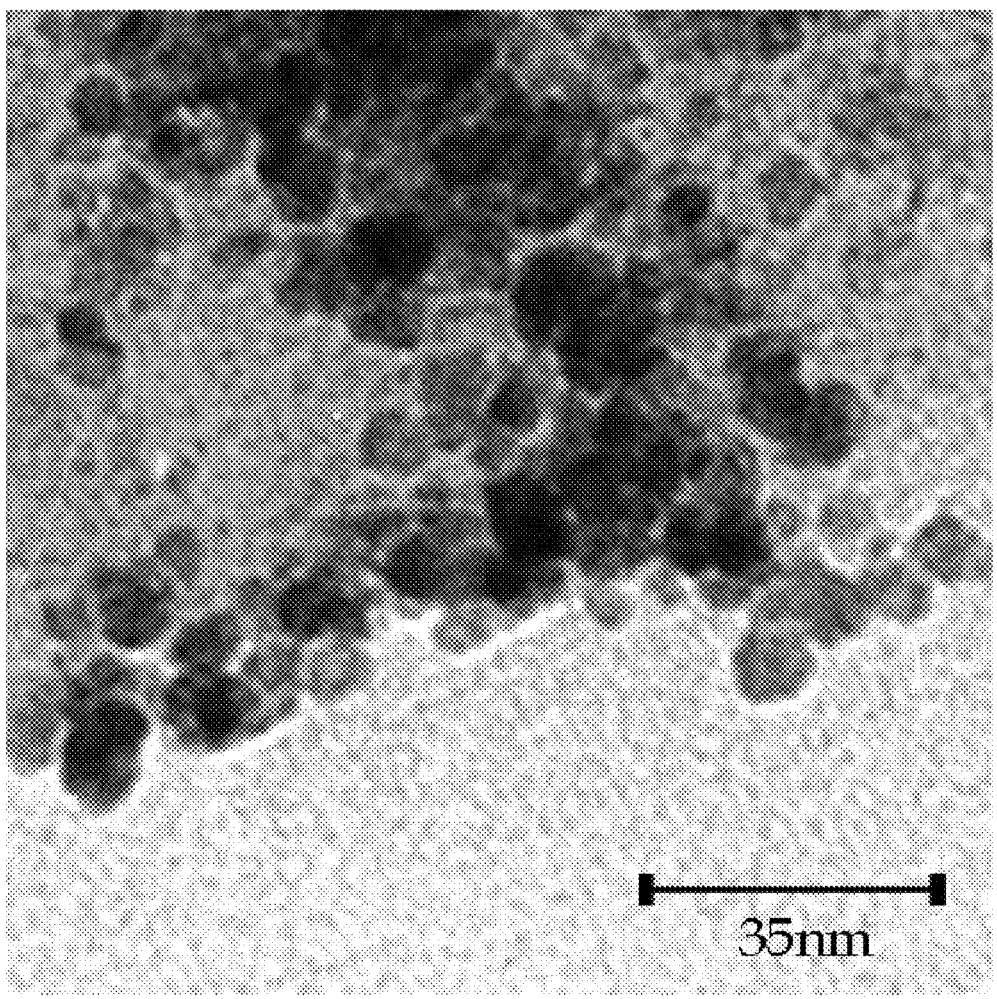
FIG. 3 illustrates the transmitting electron microscope (TEM) image of an exemplary magnetic drug-loaded polymeric particle sample, prepared as described in more detail in connection with example 1, labeled as sample 04.

FIG. 3 illustrates the transmitting electron microscope (TEM) image of a part of the surface of an exemplar magnetic drug-loaded polymeric particle. This figure shows that iron oxide nanoparticles are dispersed inside the cross-linked alginate polymer. The average size of nanoparticles is about 8.44 nm.

Figure 4:
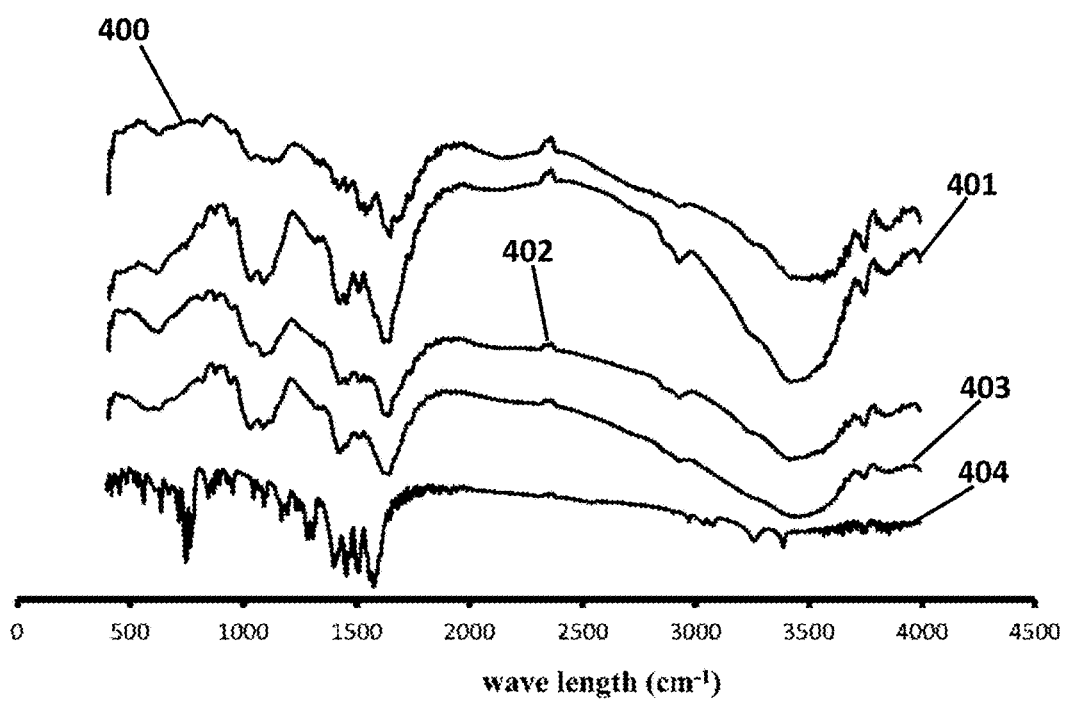
FIG. 4 illustrates Fourier transform infrared (FTIR) spectra of sodium alginate, diclofenac sodium, and samples 01, 02, and 04, prepared as described in more detail in connection with example 1.

FIG. 4 illustrates the Fourier transform infrared (FTIR) spectra of diclofenac sodium 400, sample 01 401, sample 02 402, sample 04 403, and sodium alginate 404. The characteristic absorption band of C=O, O—H and C—O of sodium alginate 404, are observed around 1640, 2350, 1200 $cm^{-1}$, respectively. The characteristic absorption bands of diclofenac sodium 400 can be observed in the spectra of the samples (—$NH_2$, —C=O, C—Cl at 3450, 1510 and 800 $cm^{-1}$, respectively), which indicates the presence of the drug in the polymeric particles. The successful encapsulation of the therapeutic agent in the polymeric carrier is confirmed based on the data illustrated in this figure.

Zeta Potential, which is the electrokinetic potential in colloidal dispersions, indicates the stability of the colloidal dispersions. Zeta potential of samples 01-04 are set forth in Table 2. Zeta potential of sample 04 shows a high negative value of −24.4 mv, which indicates that the polymeric particles are more stable in this sample.

As can be seen in Table 2, the encapsulation efficiency of samples 01 and 03 are 72%, whereas for sample 02, which is the sample prepared without the magnetic agent, the encapsulation efficiency decreases to 57%. The presence of $Fe^{2+}$ and $Fe^{3+}$ ions in the alginate solution with iron oxide nanoparticles lead to a faster and a stronger formation of gels and, therefore, the encapsulation efficiency increases in the samples containing iron oxide nanoparticles.

TABLE 2

| Sample | Size (nm) | Zeta potential (mv) | Encapsulation efficiency |
|---|---|---|---|
| Sample 01 | 417.43 ± 9.22 | −14.5 ± 2.1 | 72% ± 5.22 |
| Sample 02 | 811.54 ± 15.32 | −20 ± 3.2 | 57% ± 5.14 |
| Sample 03 | 640.89 ± 10.61 | −16 ± 2.5 | 72% ± 3.41 |
| Sample 04 | 60.29 ± 5.27 | −24.4 ± 2.7 | 64% ± 4.58 |

Magnetic properties of exemplar iron oxide nanoparticles and prepared particles (samples 01-04) are measured by a vibrating sample magnetometer (VSM) at a temperature of approximately 300 K. Hysteresis loops obtained from the aforementioned measurements show hystereses with coercivities of about 92.6954, 108.908, 101.598, 109.134 Oe, and remanences of 8.55, 1.3794, 1.7718, 1.2268 emu/g for iron oxide nanoparticles, sample 01, sample 03, and sample 04, respectively. These values indicate that samples 01, 03, and 04 have ferromagnetic behavior. In the magnetic field of 8500 Oe, the magnetizations of particles are 53.11, 8.08, 10.77 and 7.08 emu/g for iron oxide nanoparticles, sample 01, sample 03, and sample 04, respectively. The results show that as the polymer content in the sample increases, the magnetic moment of the sample decreases. Therefore, the magnetic moment of samples can be adjusted by changing the concentration of the magnetic agent (iron oxide nanoparticles) or the concentration of the polymer. For samples 01 and 04, which have the same concentration of the polymer, the magnetic moment is less for smaller particles of sample 04.

EXAMPLE 3

Drug Release Test

In this example, drug release test is performed using a dialysis bag with a molecular weight cut off of 12 KDa. Here, 12 milligrams of each of samples 01-04 is suspended in 2 ml of phosphate buffer solution (PBS) and the suspension is then placed in a dialysis bag, and the drug is transferred into a medium containing 50 ml of PBS and a 0.01% sodium azide solution, as a preservative. The containers are kept at a temperature of approximately 37° C., and are agitated at a stirrer speed of 25 rpm. The Samples are withdrawn from the container at specific intervals, and are assayed by a UV spectrophotometer. The amount of drug release from different samples, is then reported as a cumulative fractional release of the drug from each sample.

Figure 5:
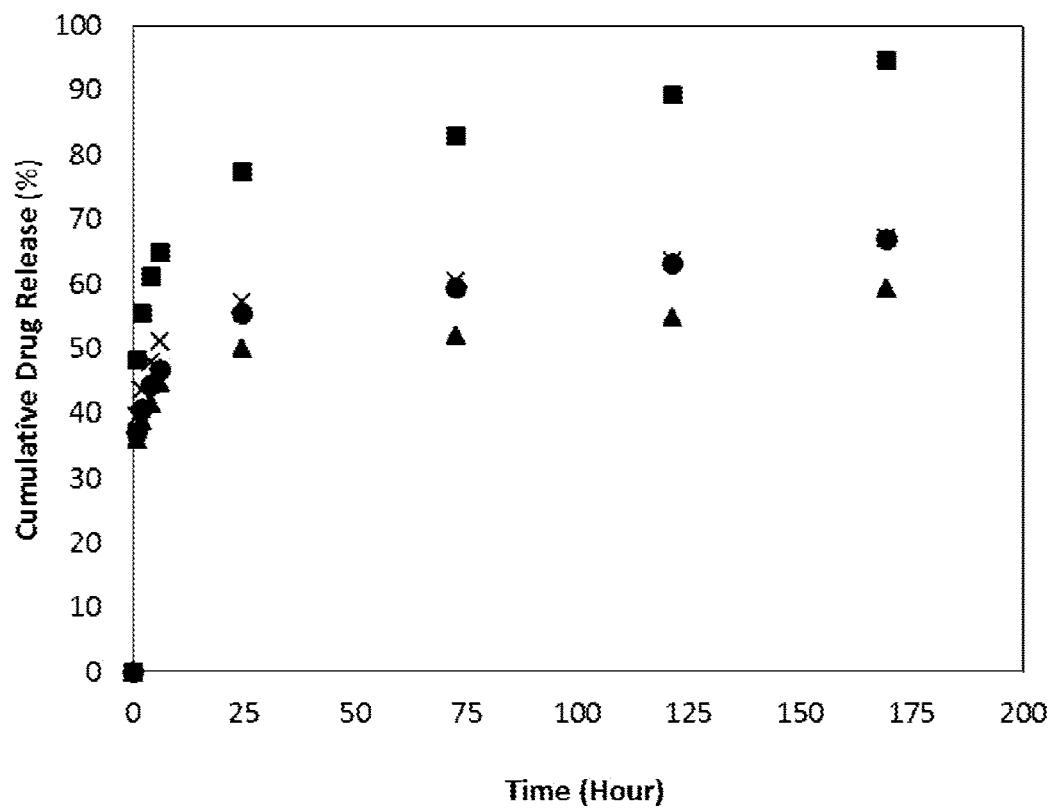
FIG. 5 illustrates the cumulative drug release from the exemplar magnetic drug-loaded particles synthesized as described in more detail in connection with example 1, versus time.

FIG. 5 shows the cumulative fractional drug release from samples 01-04 versus time. In this figure, the data corresponding to the cumulative fractional drug releases from samples 01-04 are designated by the symbols ▲, x, ■ and ●, respectively. As can be seen in this figure, sample 03 has the highest drug release rate, whereas sample 01 has the slowest drug release rate. The strength of the polymeric gel network affects the drug release rate. Since a lower concentration of the polymer is used in preparing sample 03 compared to samples 01, 02 and 04, the rate of the drug release from sample 03 is higher than that of samples 01 and 04. Sample 04 has a smaller average particle size compared to sample 01, therefore, surface to volume ratio of sample 04 is higher than that of sample 01, which leads to a higher rate of drug release from sample 04. Finally, since the presence of iron oxide inside the particles may act as a barrier of drug permeation through the chains of the polymeric network, the drug release rate from sample 02 is higher than that of sample 01.

EXAMPLE 4

Drug Transfer Through the Sclera

Figure 6:
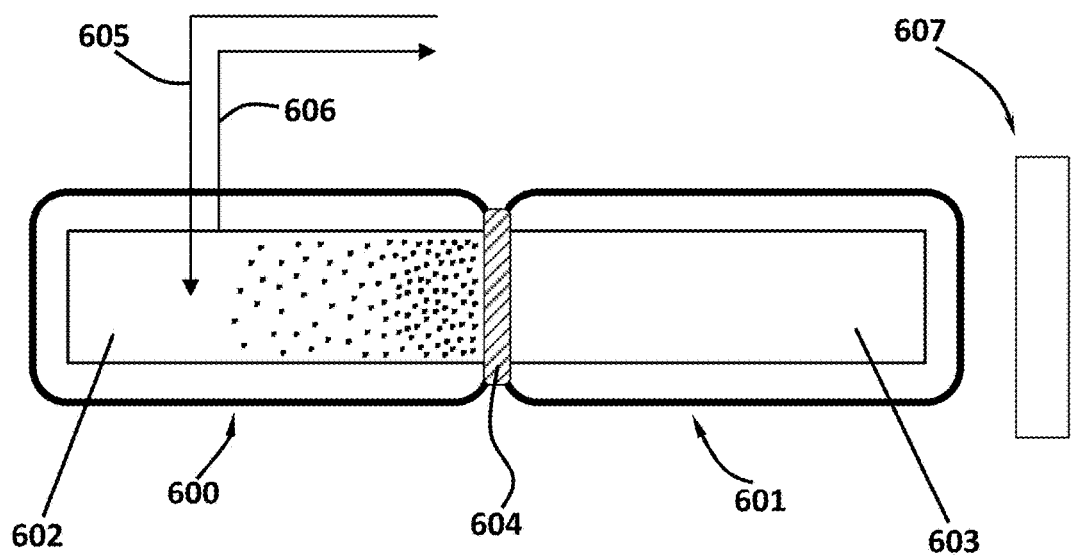
FIG. 6 is a schematic of the experimental setup described in more detail in connection with example 4.

FIG. 6 is a schematic representation of an experimental setup, which is used to simulate the periocular thermal and hydrodynamic conditions. Two side by side diffusion cells are used to simulate the periocular space 600 and the intraocular space 601. The setup includes an orbital chamber (donor chamber) 602 and a uveal chamber (receptor chamber) 603. In order to determine the drug permeation through the sclera, a sample of the sclera 604 is placed between the two diffusion cells. Before placing the sclera sample 604 between the two side by side diffusion chambers, adhering tissues on the sclera are removed by a bistoury blade, and the sclera is immediately placed in PBS. The sclera is then, cut in a square shape and is fixed between the two side by side diffusion cells, in such a way that the donor cells face the episclera side of the tissue (orbital side) and the receptor cells face the uveal side. The bulk fluid flow in the periocular space is simulated by pumping fresh PBS into the orbital chamber 602 through a line 605 specially designed for this purpose and simultaneously pumping the solution out of the orbital chamber through another line 606, and thus, simulating the bulk flow in and out of the periocular space. The extent of particle clearance from the periocular space can be determined from the amount of magnetic drug-loaded particles, which are washed out of the orbital chamber 602 through the PBS outflow line 606. The magnetic field is provided by a neodymium magnet 607 with a strength of approximately 0.6 Tesla. The contents of the diffusion chambers are held at a temperature of approximately 37° C. The magnetic drug-loaded particles, synthesized pursuant to the teachings of this application are dispersed in the PBS and 1.1 ml of the suspension is transferred to the orbital chamber (donor chamber) 602, and the uveal chamber (receptor chamber) 603 is filled with 1.1 ml of fresh PBS. The magnetic field is applied in a position that pulls the magnetic drug-loaded particles from the orbital chamber 602 towards the outer surface of the sample of sclera 604. As mentioned before, in order to simulate the clearance of the particles from the back of the eye, the orbital chamber 602 solution is removed with the rate of about 0.138 μl/s and is replaced by fresh PBS with the same rate. A UV spectrophotometer analyzer is used to determine the concentration of the drug in the uveal chamber 603 at specified time intervals. To compare the results, similar experiments are performed in the absence of the magnetic field.

Samples 01 and 04, prepared as described in more detail in connection with example 1, are used to evaluate the scleral drug transfer in the presence and the absence of a magnetic field. The aforementioned samples have different average particle sizes. Sample 01 contains larger particles, while sample 04 contains smaller particles.

Figure 7:
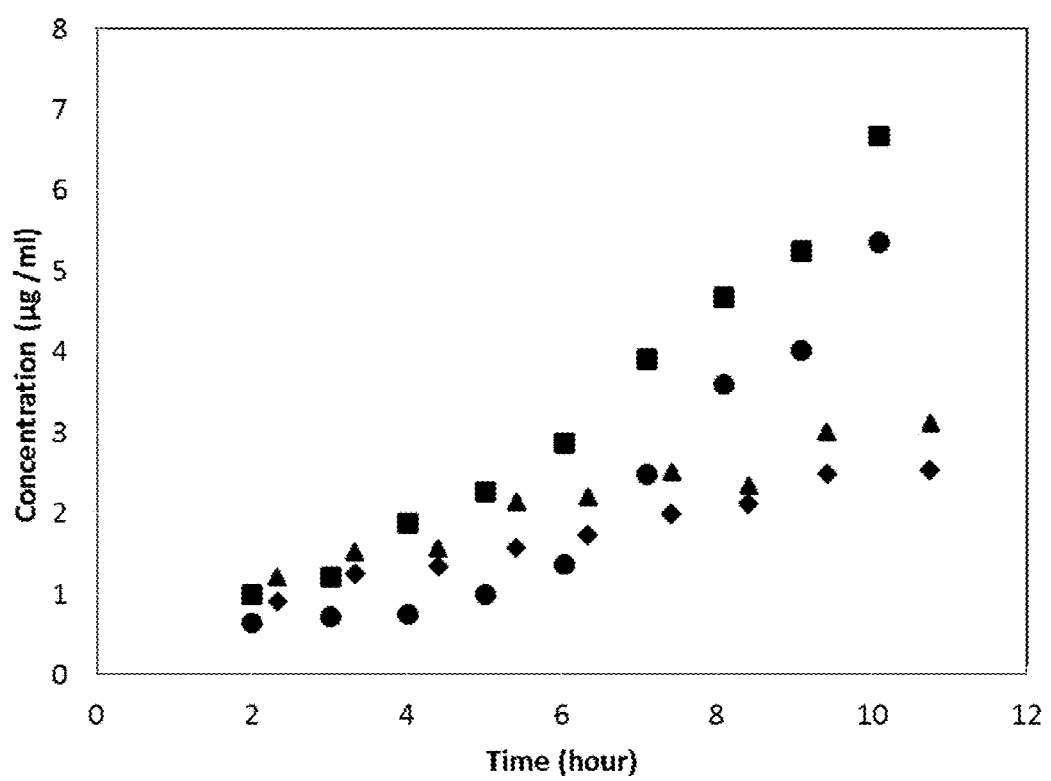
FIG. 7 illustrates the drug transfer across the sclera in the presence and absence of a magnetic field.

FIG. 7 shows the concentration of the drug in the uveal chamber (receptor chamber) 603, which is an indicator of the amount of the drug transferred through the sclera, in the presence and the absence of the magnetic field, and for the smaller and larger particles. The concentration of the drug released from the larger particles and transferred through the sclera in the presence of the magnetic field is designated by the symbol ▲; the concentration of the drug released from the smaller particles and transferred through the sclera in the presence of the magnetic field is designated by the symbol ■; the concentration of the drug released from the larger particles and transferred through the sclera in the absence of the magnetic field is designated by the symbol ◆; and the concentration of the drug released from the smaller particles and transferred through the sclera in the absence of the magnetic field is designated by the symbol ●. As can be seen in this figure, the presence of the magnetic field increases the drug transfer across the sclera by 72% and 24% for the smaller and larger particles, respectively. The clearance of the smaller particles from the periocular space (here, simulated by the orbital chamber 602) in the absence of the magnetic field is more than that of the larger particles, as they are removed by the outflow 606 easily. Accordingly, the effect of the magnetic field is more prominent for smaller particles than larger particles. Moreover, the presence of the magnetic field causes the adherence of the particles to the "orbital" surface of the sclera. Additionally, using a bio-adhesive polymer, like sodium alginate, significantly enhances this effect, and the particles adhere to the outer surface of the sclera, even when the magnetic field is removed. Therefore, in one implementation of the drug delivery system of the present application, the magnetic field is necessary for pulling the drug-loaded particles to the outer surface of the sclera, but when the particles adhere to the outer surface of the sclera due to the bio-adhesive polymer used as the carrier, the magnetic field can be removed and still the particles remain at their desirable position in the outer surface of the sclera and therapeutically effective amounts of the drug, which is encapsulated in these particles are released and transferred through the sclera.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and may be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, should may they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method for transscleral drug delivery, the method comprising steps of:
    placing magnetic drug-loaded polymeric particles in a posterior segment of an eye, outside of and adjacent to an outer surface of a sclera; and
    applying a magnetic field in front of the eye to pull the magnetic drug-loaded polymeric particles closer to the outer surface of the sclera.

2. The method according to claim 1, wherein placing the magnetic drug-loaded polymeric particles includes injecting the magnetic drug-loaded polymeric particles into the posterior segment of the eye, outside of and adjacent to the outer surface of the sclera.

3. The method according to claim 1, wherein the magnetic drug-loaded polymeric particles include a therapeutic agent and a magnetic agent encapsulated in a polymer.

4. The method according to claim 3, wherein the magnetic agent includes nanoparticles of iron oxides.

5. The method according to claim 3, wherein the polymer is selected from a group consisting of polyvinyl pyrrolidone of various molecular weights, cellulose, cellulose derivatives, cellulose esters, gums, polyethylene oxides, hyaluronic acid, carbopol polymers, chitosan, pectin, gelatin, or mixtures thereof.

6. The method according to claim 1, wherein the magnetic drug-loaded polymeric particles include a therapeutic agent and a magnetic agent encapsulated in a bio-adhesive polymer.

7. The method according to claim 6, wherein the bio-adhesive polymer is sodium alginate.

8. The method according to claim 6, wherein the therapeutic agent is selected from a group consisting of vascular endothelial growth factor (VEGF) receptor kinase inhibitors, pyrrolidine, dithiocarbamate; squalamine; TPN 470 analogue and fumagillin; protein kinase C inhibitors; thiazolidinediones; cyclooxygenase inhibitors; proteasome inhibitors; pegaptanib; vitronectin receptor antagonists; $\alpha$-v/$\beta$-3integrin antagonists; $\alpha$-v/$\beta$-1 integrin antagonists; Tie-1 and Tie-2 kinase inhibitors; interferon, including $\gamma$-interferon or interferon targeted to CNV by use of dextran and metal coordination; pigment epithelium derived factor (PEDF); endostatin; tetrathiomolybdate; angiostatin; anecortave acetate; tumistatin; acetonide; triamcinolone; RNA silencing or RNA interference (RNAi) of angiogenic factors, including ribozymes that target VEGF expression; canstatin; Isotretinoin (13-cis retinoic acid); ACE inhibitors, including but not limited to quinopril, captopril, and perindozril; inhibitors of mTOR; 3-aminothalidomide; pentoxifylline; 2-methoxyestradiol; colchicines; AMG-1470; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Verteporfin, snET2 and other photo sensitizers; inhibitors of hepatocyte growth factor; antibiotics; antiviral agents; and anesthetics.

* * * * *